United States Patent [19]

Crochemore et al.

[11] 4,102,839

[45] Jul. 25, 1978

[54] STABILIZATION OF VINYL CHLORIDE POLYMERS

[75] Inventors: Michel Crochemore, Oullin; Michel Gay, Lyons, both of France

[73] Assignee: Rhone-Poulenc Industries, Paris, France

[21] Appl. No.: 754,232

[22] Filed: Dec. 29, 1976

Related U.S. Application Data

[63] Continuation-in-part of Ser. No. 645,937, Dec. 31, 1975, abandoned.

[30] Foreign Application Priority Data

| May 10, 1976 | [FR] | France | 76 14863 |
| May 20, 1976 | [FR] | France | 76 15869 |
| May 10, 1975 | [FR] | France | 75 00765 |
| Sep. 22, 1975 | [FR] | France | 75 29466 |

[51] Int. Cl.² .............................................. C08K 5/07

[52] U.S. Cl. ....................... 260/23 XA; 260/45.75 R; 260/45.85 R; 260/45.7 R; 260/880 R; 260/897 R

[58] Field of Search .................. 260/45.75 R, 23 XA, 260/45.7 R, DIG. 43, 880, 897, 45.85

[56] References Cited

U.S. PATENT DOCUMENTS

| 3,259,597 | 7/1966 | Burger | 260/45.75 B |
| 3,396,130 | 8/1968 | Leistner et al. | 260/23 XA |
| 3,493,536 | 2/1970 | Weisfeld | 260/45.75 B |
| 3,852,227 | 12/1974 | Matsuda et al. | 260/DIG. 43 |

*Primary Examiner*—V.P. Hoke
*Attorney, Agent, or Firm*—Bacon & Thomas

[57] ABSTRACT

Vinyl chloride polymers are heat stabilized by formulating therewith minor amounts of [1] a divalent metal salt of an organic carboxylic acid and [2] either a β-diketone or a β-keto-aldehyde.

15 Claims, No Drawings

STABILIZATION OF VINYL CHLORIDE POLYMERS

This application is a continuation-in-part of application Ser. No. 645,937 filed Dec. 31, 1975 now abandoned.

BACKGROUND OF THE INVENTION

1. Field of the Invention

The present invention relates to improving the heat resistance of polymers comprised of vinyl chloride. Such polymers are typically subjected to elevated temperatures, both during the various operations for the mechanical shaping thereof and also while in use.

2. Description of the Prior Art

It is well known in the art that polymers and copolymers of vinyl chloride are utilized for the manufacture of various shaped articles by molding, extrusion and casting processes which require high temperatures in order to bring the polymer to a sufficiently soft state. At these temperatures, which can be as high as 180°-200° C., polymers based on vinyl chloride undergo considerable degradation which manifests itself in an adverse color change and in a diminution in their mechanical properties. In order to avoid these adverse changes or effects, it has been proposed to add to the polymer feed heat stabilizers such as, for example, metal chelates of dicarbonyl compounds which can be used individually or together with salts of carboxylic acids and such metals as calcium, lead and cadmium [compare U.S. Pat. Nos. 2,307,075 and 2,669,548]. Stabilizers comprising salts of heavy metals and higher fatty acids, in conjunction with certain organic phosphites [U.S. Pat. No. 2,564,646] or with certain polyols [U.S. Pat. No. 2,711,401] have also been used. However, these various means are not sufficient in the event that the polymer is to be subjected to high temperatures and is to be used for the manufacture of clear or transparent articles, because the strong heat, even though momentary or short-lived, causes the polymer to yellow to a greater or lesser extent and this renders same unsuited for certain applications. Thus, in the manufacture of films or transparent membranes, bottles, flasks, and the like, a change in the color of the polymer which would have an adverse affect on the transparency of these final products cannot be tolerated.

SUMMARY OF THE INVENTION

It has now been determined according to this invention that the vinyl chloride polymers can be stabilized against thermal degradation by formulating therewith minor amounts of the stabilizers, [1] a divalent metal salt of an organic carboxylic acid in combination with [2] a β-diketone or a β-keto-aldehyde. More particularly, the present invention provides for the heat stabilization of the vinyl chloride polymers by formulating therewith the following additives, with the noted percentages thereof being given by weight based upon the weight of the polymer feed:

[1] 0.1 to 5% of one or more divalent metal salts of an organic carboxylic acid hitherto, per se, known to be useful for the stabilization of the vinyl chloride polymers, and

[2] 0.05 to 5% of an organic dicarbonyl compound of the structural formula:

$$R_1 - CO - CHR_2 - CO - R_3 \qquad (I)$$

in which each of $R_1$ and $R_3$, which may be the same or different, represent a linear or branched alkyl or alkenyl radical having from 1 to 36 carbon atoms, an aralkyl radical having from 7 to 36 carbon atoms or an aryl or cycloaliphatic radical having less than 14 carbon atoms, said cycloaliphatic radical optionally containing one or more carbon-carbon double bonds, the aliphatic chains of said radicals optionally containing one

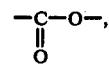

—O—, —CO— radical; one of $R_1$ or $R_3$ can represent a hydrogen atom; $R_2$ represents a hydrogen atom, a radical of the formula — CO — $R_4$, or — CO — O — $R_4$, wherein $R_4$ represents an alkyl radical having from 1 to 36 carbon atoms or an aryl radical if $R_1$ and $R_3$ are not aromatic, or a radical of the formula:

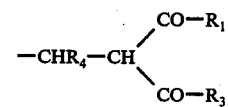

wherein $R_1$, $R_3$ and $R_4$ are as defined above;

or $R_1$ and $R_2$ together represent a divalent radical as an alkylene radical having from 1 to 12 carbon atoms or a cyclo alkylene radical having less than 14 carbon atoms, these radicals can be substituted by an aliphatic radical having from 1 to 18 carbon atoms;

in $R_1$, $R_2$ and $R_3$ the carbon atoms adjacent the indicated carbonyl groups are not doubly bonded to carbon atom and no more than one of said carbon atom is contained in an aromatic ring.

The $R_1$ and $R_3$ substituents may be substituted with a member selected from the group consisting of halo, aryl or cycloaliphatic groups having less than 14 carbon atoms, which aliphatic moieties may include — O —, — COO — or — CO — linkages within their chains.

OBJECTS OF THE INVENTION

Accordingly, it is a primary object of this invention to impart heat resistance to the vinyl chloride polymers.

Another object of the invention is the stabilization of vinyl chloride polymers against thermal degradation.

Briefly, the immediately above and other objects of the invention are attained by formulating the vinyl chloride polymers with a particular combination of stabilizing ingredients.

Other objects, features and advantages of the invention will become more apparent from the description which follows.

DETAILED DESCRIPTION OF THE PREFERRED EMBODIMENTS

In accordance with this invention a heat stabilized vinyl chloride polymer containing a heat stabilizing amount of divalent metal salt of an aliphatic or aromatic carboxylic acid and a dicarbonyl compound such as β-diketone and β-keto-aldehyde are provided. The vinyl chloride polymers that may be employed in the formulations or compositions of this invention are the resinous products obtained by the polymerization of a vinyl chloride monomer in the presence or absence of a copolymerizable monomer.

By formulations or compositions comprised of the vinyl chloride polymers, there are intended compositions or formulations containing a homopolymer or copolymer of vinyl chloride, typically in combination with the various adjuvants usually employed to facilitate processing or to provide the final product shaped articles with particular properties.

Any type of vinyl chloride homopolymer is suited for use according to the invention, no matter what its method of preparation may be, whether it be bulk polymerization, suspension polymerization, dispersion polymerization, or any other type of polymerization.

Numerous copolymers of vinyl chloride can be stabilized against the effects of heat by means which are identical to those used for the homopolymers. They comprise, for example, polymers resulting from the copolymerization of vinyl chloride with such other olefinically unsaturated comonomers polymerizable therewith as ethylene, acrylic acid esters, styrene, vinyl esters, maleic acid or anhydride, maleic acid esters, and the like.

The copolymers typically contain at least 50% by weight of vinyl chloride. However, the process according to the invention is especially well suited with respect to those copolymers which contain at least 80% by weight of vinyl chloride and in which the other monomer is vinyl acetate or vinylidene chloride. These copolymers can be used individually, or in admixture with other polymers, especially with the polyvinyl chlorides.

It is also possible according to the invention to stabilize compositions based on after-chlorinated polyvinyl chlorides, the chlorine content of which can be as high as 65 – 70% and which are very sensitive to thermal degradation when subjected to high temperatures.

The divalent metal salts [1] of the organic carboxylic acids are preferably calcium, barium, zinc, lead or cadmium salts of saturated or unsaturated aliphatic acids, or aromatic acids. Among these salts, there are mentioned the acetates, diacetates, ethylhexanoates, octoates, stearates, oleates, laurates, palmitates, myristates, ricinoleates, benzoates and phthalates. Such salts are generally employed in the form of mixtures of two, for example, a mixture of the calcium and zinc salts. It should be noted that for the manufacture of packaging for foodstuffs, or for bottles, the alkaline earth metal salts of long-chain fatty acids are very particularly well suited because of their non-toxicity and their lubricant action. The calcium and zinc stearates, laurates and 2-ethyl-hexanoates too are preferred. Amounts of these salts in the order of 0.1 to 5% relative to the weight of the polymer are limits which are compatible with the desired properties of the resultant final products.

The dicarbonyl compounds [1] utilized in conjunction with these metal salts are the β-diketones corresponding to the general structural formula I; these compounds can also be β-keto-aldehydes corresponding to the formula I when one of the radicals $R_1$ or $R_2$ is a hydrogen atom.

The subject β-diketones are known compounds which are synthesized according to such process as can be found, for example, in *Organic Reactions*, by R. Adams, 1954 edition, VIII, page 59 et seq. Certain more specific syntheses are described at *Rec. Trav. Chem. Pays-Bas*, by M. J. Kramers, 16 (1897), page 116, or at *J. Chem. Soc.*, by G. T. Morgan and E. Holmes, 127 (1925), page 2891, or at *J. Chem. Soc.*, by R. Robinson and E. Seijo (1941), page 582, or at *Chemische Berichte*, by Claisen, 20 (1887), page 2188.

The β-keto-aldehydes are prepared in accordance with conventional syntheses as can be found in *Organic Reactions*, by R. Adams et al., 8, page 59 et seq. (1954).

A conventional method for preparing certain cyclic diketones consists in reacting an ester with cyclanone or a β-tetralone in the presence of sodium, sodium amide, sodium hydrate or sodium ethylate.

These latter organic dicarbonyl compound stabilizers [2] are incorporated in amounts between 0.05 and 5%, and preferably between 0.1 and 1%, by weight, relative to the weight of polymer as aforesaid.

Representative of such compounds, there are mentioned aliphatic β-diketones, such as heptane-2,4-dione, decane-2,4-dione, ethyl nonane-2,4-dione-carboxylate and 8-methyl-non-7-ene-2,4-dione, and acyloxyacetones, such as acetylacetone, 1,1-diacetyl-acetone or triacetylmethane, stearoylacetone and stearoylalkanones. There are also mentioned the aromatic or aromatic-aliphatic β-diketones, for example, benzoylacetone, tribenzoylmethane, diacetylacetobenzenes, stearoylacetophenone and palmitoylacetophenone and 1-phenyl triacontane-1,3-dione. Diketones comprising a long-chain fatty acid radical such as stearoylacetone, palmitoylacetone and lauroylacetone or stearoylacetophenone, palmitoylacetophenone and lauroylacetophenone or cyclic diketones as stearoyl tetralone, palmitoyltetralone 2-acetyltetralone, 2-benzoyl cyclohexanone, 2-acetyl cyclohexanone or 2-acetyl cyclohexane-1,3-dione are very particularly suitable for prolonged stabilizing activity according to the invention.

Representative of the β-keto-aldehydes, there are mentioned 2-acyloxy-acetaldehydes, 2-acyloxy-propionaldehydes, and the like; thus, it is possible to employ benzoylacetaldehyde or 2-acetyl-2-methyl-acetaldehyde.

The homopolymers and copolymers of the invention can either be rigid or flexible. If rigid polymers are employed, it is possible to add thereto agents which modify their impact strength, such as, for example, the butadiene/styrene copolymers or butadiene/styrene/acrylonitrile terpolymers typically employed for improving the mechanical properties of polymers. Various adjuvants such as plasticizers, pigments, fillers, anti-oxidants, light stabilizers, and the like, can also be added to the compositions of the invention.

Other organic compounds hitherto known for their stabilizing effects, such as, for example, pentaerythritol or trihydroxyethyl isocyanurate, can also be added to the stabilizers according to the invention.

The stabilizers according to the invention can be incorporated at the same time as the other adjuvants. They can also be mixed with one another, alone or together with certain adjuvants; some then form a stabilizing composition which will subsequently be incorporated into the vinyl chloride polymer. All of the customary methods known in this field can be used for producing the mixture of the ingredients. However, homogenization of the composition or admixture can advantageously be carried out in a malaxator.

The compositions of the invention can be processed in accordance with those known techniques for working compositions of the polymers and copolymers of vinyl chloride, for example, by injection molding, extrusion, extrusion blow-molding, calendering, rotational molding, and the like.

A preferred composition of the invention takes advantage of the combination of the organic dicarbonyl stabilizer with a mixed metal salt [e.g., calcium and zinc] stabilizer to markedly retard the appearance of yellowing and to obtain finished products which are both transparent and homogeneous, and which do not suffer from exudation.

In order to further illustrate the present invention and the advantages thereof, the following specific examples are given, it being understood that same are intended merely as illustrative, and in no wise limitative.

EXAMPLES 1 to 5

A Composition A was prepared which is especially well suited for the manufacture of bottles by extrusion blow-molding.

The following mixture was prepared in a cylindrical ball mill:

|  | Grams |
|---|---|
| Poly(vinyl chloride) | 1,000 |
| Butadiene/styrene/methyl methacrylate copolymer | 100 |
| Wax E | 10 |
| Calcium stearate | 10 |
| Zinc stearate | 7 |
| Epoxidized soybean oil | 30 |
| Trinonylphenyl phosphite | 3 |

The resin composition was milled for 15 hours.

The poly(vinyl chloride) was used in powder form, characterized by a viscosity index of 80, (French Standard Specification NF T 51,013), prepared by suspension polymerization and sold under the tradename LUCOVYL RS 8000 by *RHONE-POULENC INDUSTRIES.*

Wax E is a tradename based on an ester of colophony and sold by HOECHST.

A 56 g portion of the resinous composition was a standard composition designated as Composition A. Five blends were prepared, each containing 56 grams of Composition A with additional incorporation of the organic dicarbonyl compounds by placing the mixtures in 250 cm$^3$ ball mills containing a few porcelain beads and milling for 15 hours. The following compositions were obtained:

Composition B — 0.12 g of heptane-2,4-dione having a b.p. of 180° C. at 760 mm Hg.

Composition C — 0.16 g of decane-2,4-dione.

Composition D — 0.2 g of ethyl nonane-2,4-dione carboxylate having a b.p. of 130° C. at 0.5 mm Hg.

Composition E — 0.21 g of 1-benzoyl-octan-2-one.

Composition F — 0.15 g of 2-methyl-decan-2-ene-6,8-dione having a b.p. of 234° C. at 760 mm Hg.

Sheets having a thickness of 2.5 mm were prepared by calendering the compositions at 175° C. Test samples of 10 × 20 mm were then cut from these sheets and were placed in a ventilated oven at 180° C. for varying periods of time.

The coloration of the samples were then assessed on the Gardner scale, by means of a Lovibond comparison disc.

The following results were obtained:

TABLE I

| Duration in minutes | 0 | 7 | 14 | 21 |
|---|---|---|---|---|
| Gardner number |  |  |  |  |
| Composition A | 8 | 9 | 10 | 11 |
| Composition B | 2 | 3 | 3.5 | 5 |
| Composition C | 1 | 1 | 2 | 3 |
| Composition D | 2 | 4 | 5 | 6 |

TABLE I-continued

| Duration in minutes | 0 | 7 | 14 | 21 |
|---|---|---|---|---|
| Composition E | 1 | 2 | 4 | 5 |
| Composition F | 1 | 1 | 1 | 2.5 |

From Table I it is evident that those samples which contain the organic dicarbonyl stabilizer discolored to a much lesser degree during their preparation and exhibited a much higher heat stability than standard Composition A which did not contain any dicarbonyl stabilizer.

EXAMPLES 6 to 10

Compositions H, I, K, L and M were prepared by following the procedure of Example I, utilizing 56 g batches of the Composition A' prepared in accordance with Example 1, but employing a vinyl resin of a polyvinyl chloride batch different from that of Example 1, but having the same characteristics, and respectively:

Composition H — 0.18 g of methylene-2,2'-bis-(cyclohexane-1,3-dione) having a melting point of 134° C.

Composition I — 0.15 g of benzoylacetone having a melting point of 56° C.

Composition K — 0.15 g of triacetylmethane having a b.p. of 95° C. under a pressure of 0.1 mm of mercury.

Composition L — 0.2 g of 1,4-diacetylacetobenzene having a melting point of 184° C.

Composition M — 0.2 g of 1,4-diphenyl-butane-1,3-dione.

The mixtures were milled for 15 hours.

Sheets having a thickness of 2.5 mm were prepared on a calender from these compositions, the calender rolls maintained at 180° C. The sheets were cut into 10 × 20 mm test samples. The test samples were placed in a ventilated oven at 180° C. for varying periods of time.

The coloration of the samples was then assessed on the Gardner scale, by means of a Lovibond comparison disc. The following results were obtained:

TABLE II

| Duration in minutes |  | 7 | 14 | 21 |
|---|---|---|---|---|
| Composition A' | 8 | 8 | 8 | 9 |
| Composition H | 1 | 2 | 2 | 3 |
| Composition I | 1 | 1 | 1 | 1.5 |
| Composition K | 1.5 | 2.5 | 3 | 4 |
| Composition L | 3 | 3 | 4 | 4 |
| Composition M | 1 | 1 | 1.5 | 3 |

EXAMPLE 11

A plasticized Composition Z was prepared by introducing the following constituents into a ball mill:

1,000 g of a PVC in powder form, characterized by a viscosity index equal to 120 (Standard Specification NF T 51,013) and a K value of 69, prepared by suspension polymerization and sold under the tradename LUCOVYL GS 1200 (of RHONE-POULENC INDUSTRIES)

|  | Grams |
|---|---|
| Dioctyl phthalate | 500 |
| Trinonylphenyl phosphite | 5 |
| Zinc stearate | 5.6 |
| Barium stearate | 9 |

The mixture was milled for 15 hours.

A 56 g portion of the Composition Z and 0.15 g of benzoylacetone were introduced into a 250 cm³ ball mill containing a few porcelain beads. The mixture was milled for 15 hours and a homogeneous Composition P was obtained. Test samples were prepared using the Composition P and Z, as indicated in Example 1, but the temperature of the calender rolls was maintained at 140° C.

The samples were placed in a ventilated oven at 180° C. for varying periods of time and the coloration of the samples was assessed on the Gardner scale, by means of a Lovibond comparison disc.

TABLE III

| Duration in minutes | 0 | 7 | 14 | 21 |
|---|---|---|---|---|
| Composition Z | 0 | 2 | 2 | 2 |
| Composition P | 0 | 0 | 0 | 1 |

From Table III it was determined that the samples prepared from plasticized PVC compositions are much less sensitive to yellowing than the non-plasticized samples. Moreover, the incorporation of an organic stabilizer makes it possible to reduce, very substantially, the yellowing during typical heat treatment processing of such compositions.

EXAMPLES 12 to 13

A composition of the same formulation as the Composition A of Example 1 was prepared. Blends of Composition A (56 g) to which were respectively added, Composition Q, 0.15 g of benzoylacetone; and Composition S, 0.15 g of benzoylacetone and 0.15 g of pentaerythritol, were treated in the same manner as in Example 1.

A control experiment "R" was carried out in the presence of pentaerythritol alone (0.60 g).

The results of measuring the heat stability by the Gardner scale were as follows:

TABLE IV

| Duration in minutes | 0 | 7 | 14 | 21 |
|---|---|---|---|---|
| Composition A | 6 | 7 | 8 | 8 |
| Composition Q | 1 | 1 | 2 | 3 |
| Composition S | 1 | 1 | 1.5 | 1.5 |
| Composition R | 3.5 | 4.5 | 6 | 6.5 |

From Table IV it is evident that pentaerythritol alone, even in larger amounts, is not sufficient to provide stability as good as that obtained utilizing a diketone stabilizer.

EXAMPLES 14 TO 17

A mixture consisting of:

| | Grams |
|---|---|
| Polyvinyl chloride | 800 |
| Vinyl chloride/vinyl acetate copolymer with an acetate content of 15% | 200 |
| Butadiene/styrene/methyl methacrylate copolymer | 100 |
| Epoxidized soybean oil | 30 |
| Wax E | 5 |
| Calcium stearate | 5 |
| Zinc stearate | 2.5 | was formulated in accordance with Example 1.

A 57 g portion of this mixture, to which the indicated stabilizer was added, were introduced into a ball mill pot and sheets were prepared therefrom as in Example 1.

The heat stability was measured on samples exposed to 170° C. in an oven, by Gardner colorimetry.

The following results were obtained:

TABLE V

| Duration in minutes | | 0 | 7 | 14 | 21 |
|---|---|---|---|---|---|
| Control without lactone | Gardner number | 1 | 4 | 5 | 6 |
| Benzoylacetone | 0.10 g | 0 | 0 | 1 | 3 |
| Stearoylacetone | 0.10 g | 0 | 0 | 1 | 3 |
| Stearoylacetophenone | 0.15 g | 0 | 0 | 1.5 | 3 |
| 8-Methyl-non-7-ene-2,4-dione | 0.10 g | 0 | 0 | 1.5 | 3 |

EXAMPLES 18 and 19

This example illustrates the heat stabilization of an after-chlorinated polyvinyl chloride having a chlorine content of 65%. A mixture consisting of the following was prepared:

| | Grams |
|---|---|
| After-chlorinated polymer | 1000 |
| Wax E | 10 |
| Calcium stearate | 15 |
| Zinc stearate | 1.5 |

The stabilizer was added to 57 g of this mixture and 2 mm thick small sheets were then prepared on a calender at 190° C.

Investigation of the stability, in an oven at 180° C., provided the following results:

TABLE VI

| Duration in minutes | | 0 | 7 | 14 |
|---|---|---|---|---|
| Gardner number | control | 11 | 13 | 18 |
| Stearoylacetone | 0.50 g | 6 | 10 | 11 |
| Benzoylacetone | 0.30 g | 5 | 9 | 11 |

EXAMPLES 20 to 23

Following the procedure of Example 1, 56 g portions of the Composition A were selected, to which were respectively added, 0.2 g of stearoylacetophenone, 0.2 g of palmitoylacetophenone, 0.3 g of 1-stearoyl-octan-2-one and 0.3 g of p-methoxy-stearoylacetophenone. Measurement of heat stability provided the following results:

TABLE VII

| Duration in minutes | 1 | 7 | 14 | 21 |
|---|---|---|---|---|
| Gardner number - control | 1 | 9 | 10 | 11 |
| Stearoylacetophenone | 1 | 1 | 1 | 1.5 |
| Palmotoylacetophenone | 1 | 1 | 1 | 1.5 |
| Stearoyloctanone | 1 | 1 | 1.5 | 2 |
| p-Methoxy-stearoylacetophenone | 1 | 1 | 1 | 1.5 |

EXAMPLE 24

Following the procedure of Example 1, a mixture consisting of:

| | Grams |
|---|---|
| Poly(vinyl chloride) | 1000 |
| Butadiene/styrene/methyl methacrylate copolymer | 100 |
| Wax E | 10 |
| Zinc stearate | 2.5 |
| Calcium stearate | 5 |
| Epoxidized soybean oil | 30 |
| Trinonylphenyl phosphite | 3 | was prepared.

Stearoylacetone, used in the amounts of 0.08 g [Test 1], 0.15 g [Test 2] and 0.25 g [Test 3], were added to two 56 g portions of the mixture. The results of measuring heat stability were:

TABLE VIII

| Duration in minutes | 0 | 7 | 14 | 21 | 28 | 35 |
|---|---|---|---|---|---|---|
| Control | 7 | 9 | 9 | 9 | 10 | 10 |
| Test 1 | 0 | 1 | 1.5 | 2 | 3 | 5 |
| Test 2 | 0 | 0 | 0.5 | 2 | 2 | 4 |
| Test 3 | 0 | 0 | 0 | 1 | 2 | 4 |

EXAMPLE 25

A mixture "(a)" consisting of:

|  | Grams |
|---|---|
| Poly(vinyl chloride) | 100 |
| ABS impact-resistant copolymer | 10 |
| Wax E | 1 |
| Epoxidized soybean oil | 3 |
| Zinc stearate | 0.7 |
| Calcium stearate | 1.1 |
| Decane-2,4-dione | 0.64 | was prepared.

Furthermore, a mixture "(b)" was prepared which differed from the above in that the latter two components (calcium salt and decane-2,4-dione) were replaced with 0.71 g of the calcium chelate of decane-2,4-dione. These mixtures formulated as above; the colorimetry results were as follows:

TABLE IX

| Duration in minutes | 0 | 7 | 14 | 21 |
|---|---|---|---|---|
| Gardner number - control | 8 | 8 | 8 | 8 |
| Composition (a) | 0 | 0 | 0 | 2.5 |
| Composition (b) | 1.5 | 2 | 8 | brown black |

It was observed that the two mixtures in which the molar amounts of β-diketones and calcium were substantially the same displayed a diminished stability to heat, if same were used in the form of chelates.

Results of the same order of magnitude were obtained when the zinc stearate and the decane-2,4-dione were replaced with the corresponding zinc chelate.

EXAMPLES 26 and 27

Using the composition of Example 1 and following the same procedure outlined therein, two mixtures were prepared, each containing 56 g of the standard Composition A and, respectively, 0.15 g of benzoylacetaldehyde and 0.15 g of 2-methyl-2-acetyl-acetaldehyde; using these compositions, test samples were manufactured, the Gardner number of which was measured upon treatment in a ventilated oven. The following results were obtained:

TABLE X

| Duration in minutes | 0 | 7 | 14 | 21 |
|---|---|---|---|---|
| Control composition - Gardner number | 6 | 8 | 8 | 8 |
| Benzoylacetaldehyde | 2 | 3 | 3.5 | 4 |
| 2-Methyl-2-acetyl-acetaldehyde | 3 | 5 | 5 | 5 |

From Table X is was determined that the samples which contain the organic stabilizer discolored to a much lesser extent during preparation and displayed a higher stability to the effects of heat.

EXAMPLE 28

Into a 100 ml flask provided with a stirring means a thermometer well, an ascending cooler and a dropping funnel were introduced:

5 g of methyl octacosanoate, 7.32 g of a suspension of 50% sodium hydrate in oil, and 50 ml of toluene.

The contents of the flask are heated to 60° C. 765 g of acetophenone were added dropwise over a period of 30 minutes. The mixture is then allowed to cool and was acidified by adding 10 ml of a mixture of acetic acid/water (5/5 parts by weight). The toluene-phase which stayed at a temperature of about 40° C. was separated from the aqueous phase and is washed three times with 15 ml water each. Subsequently the toluene was removed by distillation under atomspheric pressure. A crude brown colored residue (6.4 g), which melted at about 40° C. was recovered. This product was purified by recrystallization with ethanol and subsequent chromatography on a silica gel column. A white product (3.5 g) was recovered which exhibited a melting point of 88° C. ± 0.4° C.

Analysis of the white composition was determined by micro-analysis which indicated:

|  | Actual (4 tests) | Theoretical |
|---|---|---|
| Carbon | 87.75 | 82.13 |
| Hydrogen | 77.79 | 77.79 |

The above data corresponds to the formula:

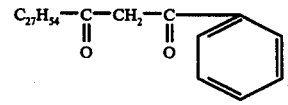

The molecular weight of 526 (theoretically 525.8) was determined by mass spectrography to the exclusion of any other "molecular" peaks. Infra-red spectrum data was consistent with the above formula.

A mixture of 0.50 g of the above product and 56 g of the Composition A, which was prepared as described in Example 7, were introduced into a 250 cm$^3$ ball mill containing several porcelain beads. The mill was turned on rollers for 15 hours and a homogeneous composition was obtained. Sheets having a thickness of 2.5 mm of the above composition were calendered at 180° C. These sheets were then cut into 10 × 20 mm samples and placed in a ventilated oven at 180° C. for varying periods of time.

The coloration of the test samples were then assessed on the Gardner scale with a Lovibond comparison disc. The following results were obtained:

TABLE XI

| Duration in minutes | 0 | 7 | 14 | 27 |
|---|---|---|---|---|
| Gardner number |  |  |  |  |
| Composition A | 8 | 9 | 10 | 77 |
| Composition of Example 28 | 7 | 7 | 7.5 | 2.5 |

EXAMPLE 29

A plasticized composition was prepared by introducing into a ball mill 1000 g of a PVC in powder form, characterized by a viscosity index equal to 120 (Standard Specification NFT 57,073) and a K value of 69, prepared by suspension polymerization and sold under the tradename LUCOVYL GS 1200, to which were added the following:

|  | Grams |
|---|---|
| Dioctyl phthalate | 500 |
| Organic aryl phosphite | 5 |
| Barium stearate | 9 |
| Zinc stearate | 5.6 |

The mill was turned on rollers for 15 hours.

A charge of 56 g of the above PVC composition and 0.5 g of the diketone product of Example 28 were introduced into a 250 cm³ ball mill containing several porcelain beads. The mill was turned on rollers for 15 hours and a homogeneous composition was obtained.

Test samples of the above PVC composition without stabilizer and test samples containing the stabilizer product of Example 28 were prepared as described in Example 1 by calendering at a temperature of 140° C.

The test samples were placed in a ventilated oven maintained at 180° C. for varying periods of time.

The coloration of the samples was assessed on the Gardner scale by means of a Lovinbond comparison disc. The following results were obtained:

TABLE XII

| Duration in minutes | 0 | 7 | 14 | 27 |
|---|---|---|---|---|
| Gardner number |  |  |  |  |
| PVC composition - no stabilizer | 0 | 2 | 3 | 3 |
| PVC composition - stabilizer of Ex. 28 | 0 | 0 | 0 | 7 |

From Table XII it can be seen that the test samples prepared from plasticized PVC compositions are much less sensitive to yellowing than non-plasticized samples. Nevertheless, the incorporation of an organic stabilizer makes it possible to further reduce very substantially the yellowing during a heat treatment corresponding to typical processing of such compositions.

EXAMPLE 30

In this example, the thermal stabilization of an afterchlorinated polyvinyl chloride containing 65% of chlorine is shown. A mixture is prepared containing:

|  | Grams |
|---|---|
| Chlorinated poly(vinyl chloride)polymer | 1000 |
| Wax E | 10 |
| Calcium stearate | 15 |
| Zinc stearate | 7.5 |

To 57 g of this mixture 0.7 g of the stabilizer of Example 28 were added.

Test samples (2 mm thickness) were prepared from both compositions similar to Example 1, except the samples were calendered at a temperature of 190° C. In stability tests conducted in an oven maintained at 180° C., the following results were obtained:

TABLE XIII

| Duration in minutes | 0 | 7 | 14 |
|---|---|---|---|
| Gardner number |  |  |  |
| Composition without stabilizer | 77 | 73 | 18 |
| Composition containing the stabilizer of Example 28 | 4 | 7 | 10 |

EXAMPLES 31 to 36

Into a 1000 ml flask provided with a stirring means a thermometer well, an ascending cooler and a dropping funnel were introduced 100 g of methyl stearate technical grade (containing methyl palmitate as an impurity).
4.05 g of a suspension containing 50% sodium hydrate in oil, and
400 ml of toluene The contents of the flask were heated to 75° to 80° C. Then over a period of 2 hours and 45 minutes, 67 g of α-tetralone were added dropwise. The temperature was maintained at 85° C. for 4 hours. The mixture was then cooled and was acidified with 230 g of a mixture of acetic acid/water/ice (80/50/100 parts by weight). The toluene phase maintained at a temperature of about 40° C. was separated from the aqueous phase and washed with 150 ml of luke warm water. This washing was repeated twice. Subsequently, the toluene was removed by distilling at atmospheric pressure. A crude brown colored residue (160.9 g), which melted at about 60° C. was recovered.

This raw product was purified by recrystallization from ethanol and 60 g of a white product consisting of stearyl tetralone and palmyl tetralone and which had a melting point of about 52° C. was recovered. Mass spectrograph analysis showed two molecular peaks corresponding to masses of 384 and 472. The NMR-spectrum corresponded to the two β-diketones obtained.

A Composition T, which is specially suited for producing bottles by extrusion blow molding, was prepared by mixing the following in a ball mill:

|  | Grams |
|---|---|
| LUCOVYL RS 8000 | 1000 |
| Butadiene/styrene/methyl methacrylate copolymer | 100 |
| Wax E | 10 |
| Calcium stearate | 10 |
| Zinc stearate | 7 |
| Epoxidized soybean oil, and | 30 |
| Trinonylphenyl phosphite | 3 |

The mixture was turned on rollers for 15 hours.

Six 250 cm³ ball mills containing several porcelain beads were each charged with 56 g of Composition T.

Five of the following carbonyl compounds were added to Composition T individually in separate ball mills in order to obtain the stabilized Compositions G, Z, N, U and V:

Composition G — 0.3 g of stearyltetralone, which was prepared according to the above described process in Example 28;

Composition Z — 0.15 g of acetyl-2-tetralone, which exhibited a melting point of 56°–57° C. and was prepared according to Example VIII of U.S. Pat. No. 2,758,077;

Composition N — 0.10 g of acetyl-2-cyclohexanone which exhibited a boiling point of 100°–115° C. and was obtained according to the method which is described in Composition Z. Am. Chem. Soc., 67, pages 1510 to 1511 (1945);

Composition U — 0.15 g of benzoyl-2-cyclohexanone, which exhibited a melting point of 88° C. and was prepared according to the method of F. W. Swaner and C. H. Hauser which is described in Composition Z. Am. Chem. Soc., 68, page 2647 (1946);

Composition V — 0.15 g of acetyl-2-cyclohexanedione-7,3.

The six ball mills were turned on rollers for 15 hours and homogeneous compositions were obtained.

Sheets of 2.5 mm thickness were prepared from these compositions by means of a calender heated to 180° C. The sheets were cut into 10 × 20 mm test samples and these samples were placed in a ventilated oven at 180° C for varying periods of time.

The coloration of the samples were then assessed on the Gardner scale by means of a Lovibond comparison disc.

The following results were obtained:

TABLE XIV

| Duration in minutes | 0 | 7 | 14 | 27 |
|---|---|---|---|---|
| Gardner number | | | | |
| Composition T | 8 | 8 | 8 | 0 |
| Composition G | 7 | 7 | 7 | 7.5 |
| Composition Z | 7.5 | 7.5 | 7.5 | 7.5 |
| Composition N | 7.5 | 7.5 | 7.5 | 2 |
| Composition U | 7.5 | 2 | 1 | 4 |
| Composition V | 7.5 | 2 | 4 | 6 |

From Table XIV is is evident that the samples which contain an organic stabilizer are much less colored during their preparation and exhibit a more significant thermal stability.

While there have been described and pointed out the fundamental novel features of the invention as applied to the preferred embodiments, those skilled in the art will appreciate that various modifications, changes, and omissions in the stabilization of vinyl chloride polymers illustrated and described can be made without departing from the spirit of the invention. It is the intention, therefore, to be limited only by the scope of the following claims.

What is claimed is:

1. In a composition of matter consisting essentially of a vinyl chloride polymer and [1] a divalent metal salt of a member selected from the group consisting of a lower aliphatic carboxylic acid, a fatty carboxylic acid and an aromatic carboxylic acid, the improvement comprising including [2] a dicarbonyl compound selected from the group consisting of β-diketones and β-keto-aldehydes having the structural formula:

$$R_1 - CO - CHR_2 - CO - R_3$$

in which each of $R_1$ and $R_3$, which may be the same or different, represents a linear or branched alkyl or alkenyl radical having from 1 to 36 carbon atoms, an aralkyl radical having from 7 to 36 carbon atoms or an aryl or cycloaliphatic radical having less than 14 carbon atoms, said cycloaliphatic radical optionally containing one or more carbon-carbon double bonds, the aliphatic chains of said radicals optionally containing one

radical, wherein one of $R_1$ or $R_3$ can represent a hydrogen atom; $R_2$ represents a hydrogen atom, a radical of the formula $$- CO - R_4 \text{ or } - CO - O - R_4,$$

wherein $R_4$ represents an alkyl radical having 1 to 30 carbon atoms or an aryl radical if $R_1$ and $R_3$ are not aromatic, or a radical of the formula:

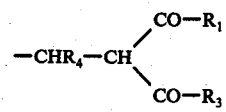

wherein $R_1$, $R_3$ and $R_4$ are as defined above; or $R_1$ and $R_2$, together represent a divalent radical selected from the group consisting of an alkylene radical having from 1 to 12 carbon atoms and a cycloalkylene radical having less than 14 carbon atoms, said radicals being unsubstituted or substituted by an aliphatic radical having from 1 to 18 carbon atoms; wherein in $R_1$, $R_2$ and $R_3$ the carbon atoms adjacent to the indicated carbonyl groups are not doubly bonded to carbon atoms and no more than one of said carbon atoms is contained in an aromatic ring; and, wherein said dicarbonyl compound [2] and said divalent metal salt [1] are present in heat stabilizing amounts, with the proviso that said dicarbonyl compound is other than diaroylmethane.

2. The composition of matter as defined by claim 1, wherein the carboxylic acid stabilizer [1] is present in an amount between 0.1 and 5% by weight, and further wherein the dicarbonyl compound [2] is present in an amount between 0.05 and 5% by weight.

3. The composition of matter as defined by claim 1, wherein the $R_1$ and $R_3$ substituents may be substituted with a member selected from the group consisting of halo, aryl or cycloaliphatic groups having less than 14 carbon atoms, which aliphatic moieties may include — CO —, — COO — or — CO — linkages within their chains.

4. The composition of matter as defined by claim 1, wherein the dicarbonyl compound (2) is a β-diketone.

5. The composition of matter as defined by claim 1, wherein the dicarbonyl compound (2) is a β-keto-aldehyde.

6. The composition of matter as defined in claim 1, wherein the carboxylic acid stabilizer [1] is selected from the group consisting of the calcium, barium, zinc, lead and cadmium acetates, ethylhexanoates, octoates, stearates, oleates, laurates, palmitates, myristates, ricinoleates, benzoates and phthalates.

7. The composition of matter as defined by claim 1, wherein the dicarbonyl compound [2] is selected from the group consisting of the aliphatic β-diketones, the acyloxyacetones, triacetylmethane, stearoylacetone, stearoylalkanone, the aromatic β-diketones, and the aromatic-aliphatic β-diketones.

8. The composition of matter as defined by claim 7, wherein the β-diketone is a stearoylacetone or a stearoylbenzophenone.

9. The composition of matter as defined by claim 1, wherein the dicarbonyl compound [2] includes a saturated or unsaturated aliphatic chain having from 14 to 30 carbon atoms.

10. The composition of matter as defined by claim 1, wherein the carboxylic acid stabilizer [1] comprises mixed metal salts of calcium and zinc, or mixed metal salts of barium and cadmium.

11. The composition of matter as defined by claim 1, wherein the vinyl chloride polymer is a homopolymer of vinyl chloride.

12. The composition of matter as defined by claim 1, wherein the vinyl chloride polymer is a copolymer of at least 50% by weight vinyl chloride and up to 50% by weight of a monoolefinically unsaturated comonomer copolymerizable therewith.

13. The composition of matter as defined by claim 12, wherein the comonomer is selected from the group consisting of ethylene, acrylic acid esters, styrene, vinyl esters, maleic acid, maleic anhydride, maleic acid esters, vinyl acetate and vinylidene chloride.

14. The composition of matter as defined by claim 13, wherein the copolymer contains at least 80% by weight vinyl chloride.

15. The composition of matter as defined by claim 1, in blended admixture with a polymer selected from the group consisting of post-chlorinated polyvinyl chloride and an impact resistant acrylonitrile-butadiene-styrene terpolymer or butadiene/styrene copolymer.

* * * * *

UNITED STATES PATENT OFFICE
CERTIFICATE OF CORRECTION

Patent No. 4,102,839          Dated  July 25, 1978

Inventor(s) Michel CROCHEMORE and Michel GAY

It is certified that error appears in the above-identified patent and that said Letters Patent are hereby corrected as shown below:

Column 14, line 32, "CO —, — COO — or — CO — should read
-- O —, — COO — or — CO —.

Signed and Sealed this

*Twenty-fourth* Day of *July 1979*

[SEAL]

*Attest:*

LUTRELLE F. PARKER

*Attesting Officer*     *Acting Commissioner of Patents and Trademarks*